United States Patent
Wang et al.

(10) Patent No.: US 6,897,190 B2
(45) Date of Patent: May 24, 2005

(54) DETERGENT COMPOSITIONS INCLUDING DISPERSIBLE POLYOLEFIN WAX AND METHOD FOR USING SAME

(75) Inventors: Jiping Wang, West Chester, OH (US); Rajan Keshav Panandiker, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 67 days.

(21) Appl. No.: 10/375,792

(22) Filed: Feb. 26, 2003

(65) Prior Publication Data

US 2003/0166495 A1 Sep. 4, 2003

Related U.S. Application Data

(60) Provisional application No. 60/360,342, filed on Feb. 28, 2002.

(51) Int. Cl.[7] .............................. C11D 1/22; C11D 1/68; C11D 3/32; C11D 3/37; D06L 1/12
(52) U.S. Cl. .................. 510/347; 510/340; 510/342; 510/351; 510/475; 510/531; 8/137
(58) Field of Search ................................. 510/340, 342, 510/347, 351, 475, 531; 8/137

(56) References Cited

U.S. PATENT DOCUMENTS

| | | | |
|---|---|---|---|
| 2,220,099 A | * | 11/1940 | Guenther et al. .............. 562/93 |
| 4,746,455 A | | 5/1988 | Matsuda et al. |
| 4,931,207 A | * | 6/1990 | Cramer et al. .......... 252/187.26 |
| 5,514,302 A | * | 5/1996 | Brown ........................ 510/280 |
| 5,830,843 A | | 11/1998 | Hartman et al. |
| 2003/0166495 A1 | * | 9/2003 | Wang et al. ................. 510/475 |

FOREIGN PATENT DOCUMENTS

| | | |
|---|---|---|
| CA | 2 311 176 | 12/2000 |
| EP | 0399445 B1 | 11/1990 |
| JP | 01-132700 A | 5/1989 |
| JP | 3074499 | 3/1991 |
| JP | 06-078557 | 10/1994 |
| JP | 2001-089713 | 4/2001 |
| WO | WO 97/28239 | 8/1997 |
| WO | WO 97/33922 | 9/1997 |
| WO | WO 01/25385 A1 | 4/2001 |
| WO | WO 01/31113 A1 | 5/2001 |

* cited by examiner

*Primary Examiner*—Brian P. Mruk
(74) *Attorney, Agent, or Firm*—Julia A. Glazer; Brahm J. Corstanje; Kim William Zerby

(57) ABSTRACT

Wash added fabric care compositions including a dispersible polyolefin wax. More particularly the present invention relates to detergent compositions including dispersible polyolefin wax. The polyolefin wax may be at least partially modified to contain various functional groups such as carboxyl, alklamide, sulfonic acid or amide groups. The polyolefin wax may be introduced in the form of a suspension, dispersion, or emulsion. A method for applying these compositions during the wash cycle of a laundry process is also included.

15 Claims, No Drawings

DETERGENT COMPOSITIONS INCLUDING DISPERSIBLE POLYOLEFIN WAX AND METHOD FOR USING SAME

CROSS REFERENCE TO RELATED APPLICATIONS

This application claims the benefit of U.S. Provisional Application No. 60/360,342 filed Feb. 28, 2002.

TECHNICAL FIELD

The present invention relates to wash added, fabric care compositions and methods for using the same during the wash cycle of a consumer laundry process. More particularly, the present invention relates to detergent compositions including dispersible polyolefin wax.

BACKGROUND OF THE INVENTION

During laundering, colored garments have a tendency to wear and fade. A portion of this color loss may be attributed to abrasion in the laundering process. This is particularly evident when utilizing automatic washing machines and automatic laundry dryers. It is also well known that fabrics/garments laundered with synthetic detergents tend to become harsher and stiffer, within a few laundry cycles as compared to when the fabric/garment is new. Fiber/fabric damage, especially after multiple laundry cycles, is also of concern to consumers.

In recent years, consumer desirability for durable press fabric garments, particularly cotton fabric garments, has risen. Durable press garments include those garments which resist wrinkling of the fabric both during wear and during the laundering process. Durable press garments can greatly decrease the hand work associated with laundering by eliminating the ironing that is sometimes necessary to prevent wrinkling of the garment. However, in most commercially available durable press fabrics, the fabric's ability to resist abrasion during laundering and in-wear is largely reduced due to the crosslinking chemistry that is used by fabrics having durable press finishes. The crosslinking chemistry tends to penetrate into and crosslink with the molecules of cellulose-containing fabrics. This in turn weakens the fabric fibers thereby reducing the tensile strength of the fibers and reducing their resistance to abrasion. The fabric's resistance to wrinkling is also reduced over time as the garment is repeatedly worn and laundered.

Accordingly, there is a need for a fabric care composition, and, in particular, a detergent composition which can provide improved color integrity, improved fabric feel, improved resistance to fabric abrasion, improved anti-wear properties, less fiber/fabric damage, and refurbish or restore anti-wrinkle properties to fabrics. Furthermore, there is a need to provide the anti-wrinkle and anti-wear properties in a single detergent composition product which can be added at the beginning of the wash cycle. This need is met by the present invention wherein an improved detergent composition is provided. The improved detergent composition of the present invention includes a dispersible polyolefin wax. The inclusion of the dispersible polyolefin wax allows for delivery of better color integrity, better fabric feel, less fiber/fabric damage, better anti-wrinkling, and better anti-wear properties to the garment during the wash cycle. Furthermore, in comparison to fabrics treated with crosslinking chemistry, use of the dispersible polyolefin wax of the present invention will not adversely impact tensile strength or abrasion resistance. Yet further, it is thought that use of the dispersible polyolefin wax of the present invention may improve the abrasion resistance of fabric.

SUMMARY OF THE INVENTION

The present invention relates to a laundry detergent composition comprising from about 1% to 80% by weight of a detersive surfactant, from about 0.1% o 80 by weight of a detergent builder, and from about 0.01% to 50% by weight of a dispersible polyolefin wax. The polyolefin wax may be polyethylene wax, polypropylene wax, or a mixture thereof. The polyolefin wax can be partially modified to contain functional groups including but not limited to carboxyl, alkylamide, sulfonic acid, amide, or mixtures thereof.

The polyolefin wax may be added to the laundry detergent composition in the form of an emulsion or suspension wherein the emulsion or suspension comprises from about 0.05% to 60% by weight of the polyolefin wax. Typically the ratio of emulsifier to dispersible polyolefin wax is from about 1:100 to 1:2.

The invention also relates to a laundry detergent composition comprising from about 0.01% to 50% by weight of a dispersible polyolefin wax wherein the laundry detergent composition increases the Fabric Angle of Recovery at least about 5 degrees. The invention further relates to a laundry detergent composition comprising from about 0.01% to 50% by weight of a dispersible polyolefin wax wherein the polyolefin wax has a wax dropping point of from about 30 to 150° C. and an acid number from about 5 to about 200 KOH mg/g.

All percentages, ratios and proportions herein are on a weight basis unless otherwise indicated. All documents cited herein are hereby incorporated by reference.

DETAILED DESCRIPTION OF THE INVENTION

Laundry Detergent Compositions

The present invention relates to wash added, fabric care compositions which contact the fabric during the wash cycle. These fabric care compositions improve color integrity, fabric feel, abrasion resistance and wrinkle reduction of fabrics to which they are applied. The laundry detergent compositions of the present invention include detersive surfactant, detergent builder, and a dispersible polyolefin wax which serve to enhance fabric appearance and fabric tactile properties. The detergent products of the present invention may be in the form of a solid (non-limiting examples of which include granules, powders, tablets, bars, and the like) or a liquid.

The detergent products of the present invention typically have a pH from about 7–11. For liquid detergents the pH is preferably from about 7–8.5. For solid detergents the pH is preferably from about 9–11. Optional components of the present invention include but are not limited to conventional detergent components such as bleaches and bleach activators, enzymes and enzyme stabilizing agents, suds boosters or suds suppressers, anti-tarnish and anticorrosion agents, non-builder alkalinity sources, chelating agents, organic and inorganic fillers, solvents, hydrotropes, optical brighteners, dyes, perfumes, modified cellulose ether fabric treatment agents, and deposition aids. Detergent compositions of the present invention may be made in accordance with U.S. Pat. Nos. 6,274,540 and 6,306,817 and WIPO Publication Nos. WO 01/16237 published Mar. 8, 2001 and WO 01/16263 published on Mar. 8, 2001.

I. Detersive Surfactant

The detergent compositions herein essentially comprise from about 1% to 80% by weight of a detersive surfactant.

Preferably such compositions comprise from about 5% to 50% by weight of this surfactant. Detersive surfactants utilized can be of the anionic, nonionic, zwitterionic, ampholytic or cationic type or can comprise compatible mixtures of these types. Preferably the detersive surfactants are anionic, nonionic or a mixture thereof. Most preferably, the detersive surfactants are anionic. Detergent surfactants useful herein are described in U.S. Pat. No. 3,664,961, Norris, issued May 23, 1972, U.S. Pat. No. 3,919,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980.

Useful anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional non-soap anionic surfactants which are suitable for use herein include the water-soluble salts, preferably the alkali metal, and ammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are a) the sodium, potassium and ammonium alkyl sulfates, especially those obtained by sulfating the higher alcohols ($C_8$–$C_{18}$ carbon atoms) such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11-13}$ LAS.

Preferred nonionic surfactants are those of the formula $R^1(OC_2H_4)_nOH$, wherein $R^1$ is a $C_{10}$–$C_{16}$ alkyl group or a $C_8$–$C_{12}$ alkyl phenyl group, and n is from 3 to about 80. Particularly preferred are condensation products of $C_{12}$–$C_{15}$ alcohols with from about 5 to about 20 moles of ethylene oxide per mole of alcohol, e.g., $C_{12}$–$C_{13}$ alcohol condensed with about 6.5 moles of ethylene oxide per mole of alcohol.

Additional suitable nonionic surfactants include polyhydroxy fatty acid amides of the formula:

wherein R is a $C_{9-17}$ alkyl or alkenyl, $R_1$ is a methyl group and Z is glycidyl derived from a reduced sugar or alkoxylated derivative thereof. Examples are N-methyl N-1-deoxyglucityl cocoamide and N-methyl N-1-deoxyglucityl oleamide. Processes for making polyhydroxy fatty acid amides are known and can be found in Wilson, U.S. Pat. No. 2,965,576 and Schwartz, U.S. Pat. No. 2,703,798, the disclosures of which are incorporated herein by reference.

II. Detergent Builder

The detergent compositions herein also essentially comprise from about 0.1% to 80% by weight of a detergent builder. Preferably such compositions in liquid form will comprise from about 1% to 10% by weight of the builder component. Preferably such compositions in granular form will comprise from about 1% to 50% by weight of the builder component. Detergent builders are well known in the art and can comprise, for example, phosphate salts as well as various organic and inorganic nonphosphorus builders.

Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other suitable polycarboxylates for use herein are the polyacetal carboxylates described in U.S. Pat. No. 4,144,226, issued Mar. 13, 1979 to Crutchfield et al, and U.S. Pat. No. 4,246,495, issued Mar. 27, 1979 to Crutchfield et al, both of which are incorporated herein by reference. Particularly preferred polycarboxylate builders are the oxydisuccinates and the ether carboxylate builder compositions comprising a combination of tartrate monosuccinate and tartrate disuccinate described in U.S. Pat. No. 4,663,071, Bush et al., issued May 5, 1987, the disclosure of which is incorporated herein by reference.

Examples of suitable nonphosphorus, inorganic builders include the silicates, aluminosilicates, borates and carbonates. Particularly preferred are sodium and potassium carbonate, bicarbonate, sesquicarbonate, tetraborate decahydrate, and silicates having a weight ratio of $SiO_2$ to alkali metal oxide of from about 0.5 to about 4.0, preferably from about 1.0 to about 2.4. Also preferred are aluminosilicates including zeolites. Such materials and their use as detergent builders are more fully discussed in Corkill et al, U.S. Pat. No. 4,605,509, the disclosure of which is incorporated herein by reference. Also, crystalline layered silicates such as those discussed in Corkill et al, U.S. Pat. No. 4,605,509, incorporated herein by reference, are suitable for use in the detergent compositions of this invention.

III. Polyolefin Wax

The laundry detergent compositions of the present invention also include a dispersible polyolefin wax. Preferably, the polyolefin wax is polyethylene wax, polypropylene wax, or mixtures thereof. The polyolefin wax may be at least partially modified to contain various functional groups, such as carboxyl, alkylamide, sulfonic acid or amide groups. More preferably, the polyolefin wax employed in the present invention is at least partially carboxyl modified or, in other words, oxidized. In particular, oxidized or carboxyl modified polyethylene wax is preferred in the compositions of the present invention.

For ease of formulation, the dispersible polyolefin wax is preferably introduced as a suspension, dispersion, or an emulsion of polyolefin wax dispersed by use of an emulsifying agent. The polyolefin wax suspension, dispersion, or emulsion comprises from about 0.5% to about 60%, preferably from about 5 to about 45% by weight, and more preferably from about 10 to about 40% by weight of polyolefin wax. The polyolefin wax has a wax dropping point (see ASTM D3954-94, volume 15.04—"Standard Test Method for Dropping Point of Waxes") of from about 30 to 150° C., preferably from about 40 to 130° C., and more preferably from about 45 to 120° C. The polyolefin wax has an acid number from about 5 to 200 mg/g KOH and preferably from about 10 to 100 mg/g KOH (wherein the acid number indicates the mg of KOH needed to neutralize 1 g of polyolefin wax). Suitable polyolefin waxes are available commercially from suppliers including but not limited to Honeywell (A-C polyethylene), Clariant (Velustrol emulsion), BASF (LUWAX), and Michelman Incorporated.

When a dispersion, suspension, or emulsion is employed, the emulsifier and/or dispersing agent may be any suitable emulsification agent including anionic, cationic or nonionic surfactants or mixtures thereof. Most any suitable surfactant may be employed as the emulsifier of the present invention. Preferably the emulsifier and/or dispersing agent is anionic, nonionic, or a mixture thereof. Most preferably the emulsifier and/or dispersing agent is anionic. The dispersible polyolefin wax is dispersed by use of an emulsifier or suspending agent in a ratio of emulsifier to polyolefin wax of from about 1:100 to about 1:2. Preferably, the ratio ranges from about 1:80 to 1:5 and more preferably from about 1:50 to 1:8. The suspension, dispersion, or emulsion of polyolefin wax has a mean particle size diameter of from about 5 nm to 5 $\mu$m. Preferably, the mean particle size diameter is from about 10 nm to 500 nm. More preferably, the mean particle size diameter is from about 15 nm to about 100 nm. A suitable instrument for measuring particle size diameter is a Horiba LB-500.

The detergent compositions of the present invention may contain from about 0.01% to about 50% by weight of the polyolefin wax. Preferably, the compositions include from about 0.5% to about 20% by weight polyolefin wax, and more preferably from about 0.5% to about 10% by weight polyolefin wax. When the dispersible polyolefin wax is added as an emulsion, dispersion, or suspension of polyolefin wax as described above, from about 0.5% to about 60%, and more preferably from about 1% to about 40% by weight of the emulsion, dispersion, or suspension may be added to the detergent.

Particularly preferred compositions according to the present invention include those polyolefin wax emulsions which increase the Fabric Angle of Recovery at least about 5 degrees and preferably at least about 10 degrees when compared with the control described in the method section of this document (i.e.; method entitled "Measurement of Fabric Angle of Recovery").

IV. Optional Detergent Ingredients

In addition to the surfactants, builders, and polyolefin wax, the detergent compositions of the present invention can also include any number of additional optional ingredients. These include detergent composition components such as modified cellulosic polymers, bleaches and bleach activators, enzymes, and enzyme stabilizing agents, suds boosters or suds suppressers, anti-tarnish and anticorrosion agents, soil suspending agents, soil release agents, germicides, pH adjusting agents, non-builder alkalinity sources, chelating agents, organic and inorganic fillers, solvents, hydrotropes, optical brighteners, dyes, and perfumes.

1. Modified Cellulosic Polymers

An optional modified cellulosic polymer may be included in the detergent compositions of the present invention. Such materials have been found to impart a number of appearance benefits to fabrics and textiles laundered in aqueous washing solutions formed from detergent compositions which contain such modified cellulosic materials. Such fabric appearance benefits can include, for example, improved overall appearance of the laundered fabrics, reduction of the formation of pills and fuzz, protection against color fading, improved abrasion resistance, etc. The modified cellulosic polymers used in the compositions and methods herein can provide such fabric appearance benefits with acceptably little or no loss in cleaning performance provided by the laundry detergent compositions into which such materials are incorporated.

The modified cellulosic polymers useful herein may be of the nonionic, cationic or anionic types, or the modified cellulosic polymeric component of the compositions herein may comprise combinations of these cellulosic polymer types. The modified cellulosic polymer component of the compositions herein will generally comprise from about 0.1% to 8% by the weight of the composition. More preferably, such modified cellulosic materials will comprise from about 0.5% to 4% by weight of the compositions, most preferably from about 1% to 3%.

One suitable type of modified cellulosic polymer for use herein comprises hydrophobically-modified, nonionic cellulose ethers having a molecular weight of from about 10,000 to 2,000,000, preferably from about 50,000 to 1,000,000.

2. Bleaches and Bleach Activators

A preferred optional ingredients for incorporation into the detergent compositions herein comprises a bleaching agent, e.g., a peroxygen bleach. Such peroxygen bleaching agents may be organic or inorganic in nature. Inorganic peroxygen bleaching agents are frequently utilized in combination with a bleach activator.

Useful organic peroxygen bleaching agents include percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. No. 4,483,781, Hartman, Issued Nov. 20, 1984; European Patent Application EP-A-133,354, Banks et al., Published Feb. 20, 1985; and U.S. Pat. No. 4,412,934, Chung et al., Issued Nov. 1, 1983. Highly preferred bleaching agents also include 6-nonylamino-6-oxoperoxycaproic acid (NAPAA) as described in U.S. Pat. No. 4,634,551, Issued Jan. 6, 1987 to Burns et al.

Inorganic peroxygen bleaching agents may also be used, generally in particulate form, in the detergent compositions herein. Inorganic bleaching agents are in fact preferred. Such inorganic peroxygen compounds include alkali metal perborate and percarbonate materials. For example, sodium perborate (e.g. mono- or tetra-hydrate) can be used. Suitable inorganic bleaching agents can also include sodium or potassium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used. Frequently inorganic peroxygen bleaches will be coated with silicate, borate, sulfate or water-soluble surfactants. For example, coated percarbonate particles are available from various commercial sources such as FMC, Solvay Interox, Tokai Denka and Degussa.

Inorganic peroxygen bleaching agents, e.g., the perborates, the percarbonates, etc., are preferably combined with bleach activators, which lead to the in situ production in aqueous solution (i.e., during use of the compositions herein for fabric laundering/bleaching) of the peroxy acid corresponding to the bleach activator.

3. Enzymes and Enzyme Stabilizing Agents

Another highly preferred optional ingredient in the detergent compositions herein is a detersive enzymes component. Enzymes can be included in the present detergent compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, cellulases, peroxidases, and mixtures thereof of any suitable origin, such as vegetable, animal, bacterial, fungal and yeast origin.

"Detersive enzyme", as used herein, means any enzyme having a cleaning, stain removing or otherwise beneficial effect in a laundry detergent composition.

Enzymes are normally incorporated into detergent compositions at levels sufficient to provide a "cleaning-effective amount". The term "cleaning-effective amount" refers to any amount capable of producing a cleaning, stain removal, soil removal, whitening, deodorizing, or freshness improving effect on substrates such as fabrics. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation.

The enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

The detergent compositions of the present invention can provide numerous benefits to laundered garments or fabrics as opposed to prior art compositions. These benefits include improved fabric feel, improved anti-wrinkling, improved ease-of-ironing, improved color appearance and improved abrasion resistance. Furthermore, the consumer can achieve this benefit through a single delivery system (i.e.; the detergent composition) versus the prior art which required delivery via a fabric softening system added to the rinse cycle of the laundry process.

The compositions of the present invention may also provide wrinkle reduction properties to garments or fabrics. Through the use of the compositions of the present invention, wrinkle reduction properties can be provided to garments which have not been previously treated with a wrinkle reducing agent. In addition, the compositions of the present invention may restore or refurbish the wrinkle reduction properties to garments or fabrics which have previously been treated with a wrinkle reducing agent or, in other words, durable press garments. Fabrics, especially cotton, have a tendency to wrinkle during the laundering process. Wrinkling is caused at the fiber level by the inability of the fibers to readily slip past one another in response to stresses applied to the fabric during laundering. The fibers can become "stuck" in the wrong configuration, thus leading to a wrinkle on the macroscopic level.

While not wishing to be bound by theory, it is believed that the polyolefin wax in the composition described herein serves as a lubricant between fibers, allowing them to slip past one another more easily. Thus, during laundering, the fabrics have a decreased propensity to wrinkle. To the consumer, the end result is garments which are less wrinkled at the end of the laundering event. Therefore, less ironing is required for the consumer to achieve the desired end result. In fact, some items of clothing may no longer need to be ironed as a result of treatment with the compositions herein. For those treated items that are still ironed, less time is required and the task is made easier due to the lubrication properties of the polyolefin. Hence, it is the inclusion of the dispersible polyolefin which provides the primary anti-wrinkling effect.

The compositions of the present invention provide a color appearance benefit. That is, the compositions of the present invention can improve the overall appearance of fabrics which are treated in the compositions of the present invention. This improved color appearance can be manifested in simple overall appearance of the fabrics or in the reduction of pilling. Colored fabrics have a tendency to lose color and become duller in appearance as a result of multiple launderings. One mechanism by which fabrics lose color is abrasion. Fabrics moving past one another and against the washing machine tub during laundering tend to "rough-up" their surfaces, resulting in microfibrils appearing on the surface of the fibers in the garment. Macroscopically, this appears as "fuzzing" or "dulling" of the color of the item. Furthermore, fabrics may begin to fray (wear), especially around seams, by a similar mechanism as a result of repeated launderings.

While not wishing to bound by theory, the use of lubricants such as polyolefins dispersed in a laundry composition, decreases the frictional forces encountered by the fabrics during the laundering process, thereby decreasing the fuzzing and fraying of the fibers. To the consumer, treated garments have colors more true to their original condition and appear less "worn-out" after multiple washings. The benefit of color appearance improvement is present in the polyolefin wax-containing detergent compositions described above.

The use of lubricants such as a polyolefin wax in a laundry composition also make fabrics softer and smoother due to reduced friction between fiber-fiber and yarn-yarn. This improves fabric feel after the laundering process.

Accordingly, the present invention also comprises a method for laundering fabrics or garments by contacting the fabrics or garments with the compositions of the present invention. The following examples illustrate the compositions of this invention, but are not intended to be limiting thereof.

METHODS AND EXAMPLES

Measurement of Fabric Angle of Recovery

1. Collection of Fabric Swatches

All swatches for testing are purchased new from Test Fabrics Inc. They are washed in AATCC standard reference detergent, followed by 2 cycles of clear rinse. The following quantities of the specified swatches are used for testing. Enough 50/50 cotton/polyester pillowcases should be used to make the dry load weight equal 5.5 lbs:

| Garment | Composition | Swatch Wt. (g) | Quantity |
|---|---|---|---|
| Cotton Twill Fabric Pocket (16" × 20") | 100% Cotton | 45 | 2 |

*Cotton twill swatches purchased from Test Fabrics, Inc. Catalog # 49

2. Swatch Soaking Procedure

Into a 400 ml beaker, 68 g water is added. To this is added 0.383 g active of the polyolefin wax emulsion. This is then mix well. Two 45 g swatches are added into the solution. The swatches are allowed to fully absorb all of the solution. The swatches are then wrung out, and the procedure repeated until the fabric is thoroughly wetted with the solution and all the solution is absorbed by the swatches. The soaked swatches are allowed to sit for 2 hours. After the 2 hour period, all the swatches are placed into a clean, empty washer on the spin setting and spun for 4 minutes.

For the control samples, the same procedure as above is followed, except that no polyolefin wax emulsion is added.

3. Swatch Drying

The swatches are removed from the washer and placed into a preheated dryer for 45 minutes. The dryer also contains the appropriate amount of pillowcases, that had gone through the rinse cycle, and are still wet. Upon completion of drying, the swatches are removed and hung in a constant temperature/humidity room having a relative humidity of 40% and at temperature of 70° F.

4. Sample Preparation and Angle Recovery Determination

Referring to AATCC Test Method 66-1998 "Wrinkle Recovery of Woven Fabrics: Recovery Angle" the method of which is incorporated herein by reference, the current procedure deviates from AATCC Test Method 66-1998 in that the relative humidity of the current procedure is 40% instead of 65%.

EXAMPLES

| Type Polyolefin Wax Used | Wax Dropping Point (° C.) | Acid # mg KOH/g | Type Emulsifier | Average Particle Size Diameter (nm) | Product Trade Name* | Recovery Angle |
|---|---|---|---|---|---|---|
| Oxidized polyethylene | 101 | 14–17 | nonionic | 45 | ME68725 | Δ21 |
| Oxidized polyethylene | 101 | 14–17 | cationic | 50 | ME03430 | Δ23 |
| Oxidized polyethylene | 136 | 24–27 | nonionic | 35 | ME32535 | Δ11 |
| Oxidized polyethylene | 88 | 14–17 | nonionic | 40 | ME07430 | Δ5 |
| Polyethylene | 90 | Nil | nonionic | 40 | ME41740 | Δ12 |
| Ethylene Acrylic Acid copolymer | 105 | 37–44 | nonionic | 50 | ME02925 | Δ12 |

*Polyolefin wax-based emulsion products available from Michelman Incorporated of Cincinnati, Ohio.

Polyolefin Wax Emulsion in Detergent Compositions

Examples of Liquid Detergent with Polyolefin Wax Emulsion

| Ingredient | Example 1 Wt % | Example 2 Wt % |
|---|---|---|
| C12–15 alkyl polyethoxylate sulfate | 12.31 | 12.31 |
| Linear alkylbenzene sulfonate | 5.39 | 5.39 |
| Ethanol | 3.44 | 3.44 |
| Monoethanolamine | 1.49 | 1.49 |
| Propandiol | 6.61 | 6.61 |
| C12–13 Alkyl polyethoxylate (9) | 2.18 | 2.18 |
| C12–14 alkyl dimethylamine N-oxide | 0.73 | 0.73 |
| C12–14 fatty acid | 1.98 | 1.98 |
| Citric acid | 3.96 | 3.96 |
| Borax | 1.50 | 1.50 |
| Sodium hydroxide (to pH 8.0) | 5.00 | 5.00 |
| Polyethylene Wax emulsion 1* | 2.00 (based on wax content of emulsion) | — |
| Polyethylene Wax emulsion 2** | — | 1.50 (based on wax content of emulsion) |
| Water, perfume, enzymes, suds suppressor, brightener, deposition aid & other optional ingredients | to 100% | to 100% |

*Using oxidized Polyethylene wax (obtained from Clariant Incorporated of Germany), having an acid number of 14–17 KOH mg/g, a wax dropping point of 76° C., emulsified with an anionic emulsifier, the emulsified polyethylene wax having a mean particle size diameter of 35 nm.
*Using oxidized Polyethylene wax (ME68725 obtained from Michelman Incorporated of Cincinnati, Ohio) having an acid number of 14–17 KOH mg/g, a wax dropping point of 101° C., emulsified with a nonionic emulsifier, the emulsified polyethylene wax having a mean particle size diameter of 40 nm.

Examples of Powder Detergent with Polyolefin Wax Emulsion

| Ingredient | Example 1 Wt % | Example 2 Wt % |
|---|---|---|
| C12 linear alkylbenzene sulfonate | 3.44 | 3.44 |
| C16–17 methyl branched alkyl sulfate | 9.41 | 9.41 |
| C14–15 alkyl sulfate | 4.04 | 4.04 |
| AlSil | 37.37 | 37.37 |
| $Na_2CO_3$ | 22.34 | 22.34 |
| PEG | 2.53 | 2.53 |
| DTPA | 0.72 | 0.72 |
| NaPAA | 1.03 | 1.03 |
| Perborate | 2.56 | 2.56 |
| Nonanoyloxybenzenesulfonate | 1.92 | 1.92 |
| Modified cellulose | 1.54 | 1.54 |
| Polyethylene emulsion 1* | 2.00 (based on wax content of emulsion) | — |
| Polyethylene emulsion 2** | — | 2.50 (based on wax content of emulsion) |
| Water, perfume, enzymes, suds suppressor, brightener, deposition aid & other optional ingredients | to 100% | to 100% |

*Using oxidized Polyethylene wax (obtained from Clariant Incorporated of Germany), having an acid number of 14–17 KOH mg/g, a wax dropping point of 76° C., emulsified with an anionic emulsifier, the emulsified polyethylene wax having a mean particle size diameter of 35 nm.
**Using oxidized Polyethylene wax (ME68725 obtained from Michelman Incorporated of Cincinnati, Ohio) having an acid number of 14–17 KOH mg/g, a wax dropping point of 101° C., emulsified with a nonionic emulsifier, the emulsified polyethylene wax having a mean particle size diameter of 40 nm.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. All documents cited within the Detailed Description herein are, in relevant part, incorporated by reference. The citation of any document is not to be construed as an admission that it is prior art with respect to the present invention.

What is claimed is:

1. A laundry detergent composition comprising:
   (A) from about 1% to 80% by weight of a detersive surfactant; wherein said detersive surfactant is a straight chain or branched sodium or potassium alkylbenzene sulfonates in which the alkyl group contains from about 9 to 15 carbon atoms; polyhydroxy fatty acid amides of the formula;

wherein R is a $C_{9-17}$ alkyl or alkenyl, $R_1$ is a methyl group and Z is glycidyl derived from a reduced sugar or alkoxylated derivative thereof, or mixtures thereof;
   (B) from about 0.1% to 80% by weight of a detergent builder; and
   (C) from about 0.01% to 50% by weight of a dispersible polyolefin;
wherein said laundry detergent composition is added to the wash cycle of a laundry process.

2. The laundry detergent composition of claim 1 wherein said polyolefin is polyethylene, polypropylene, or a mixture thereof.

3. The laundry detergent composition of claim 1 wherein said polyolefin is partially modified to contain functional groups, wherein said functional groups are carboxyl, alkylamide, sulfonic acid, amide or mixtures thereof.

4. The laundry detergent composition of claim 3 wherein said polyolefin is partially carboxyl modified polyethylene or oxidized polyethylene.

5. The laundry detergent composition of claim 1 wherein said dispersible polyolefin is added to said laundry detergent composition as an emulsion, dispersion, or a suspension in a ratio of emulsifier to said dispersible polyolefin of from about 1:100 to about 1:2.

6. The laundry detergent composition of claim 5 wherein said emulsion, dispersion, or suspension comprises from about 1 to 60% by weight of said dispersible polyolefin.

7. The laundry detergent composition of claim 5 wherein said dispersible polyolefin emulsion, dispersion, or suspension comprises from about 0.5% to 60% by weight of said laundry detergent composition.

8. The laundry detergent composition of claim 5 wherein said dispersible polyolefin emulsion, dispersion, or suspension increases the Fabric Angle of Recovery about 5 degrees.

9. The laundry detergent composition of claim 5 wherein said emulsion, dispersion, or suspension has a mean particle size diameter of from about 5 nm to 5 µm.

10. The laundry detergent composition of claim 1 wherein said dispersible polyolefin has a wax dropping point of from about 30 to 150° C.

11. The laundry detergent composition of claim 1 wherein said dispersible polyolefin has an acid number from about 5 to 200 mg/g KOH.

12. A method for treating fabrics during the wash cycle of a laundry process, said method comprising the steps of:
   a) providing a laundry detergent composition wherein said laundry detergent composition comprises:
      (i) from about 1% to 80% by weight of a detersive surfactant; wherein said detersive surfactant is a straight chain or branched sodium or potassium alkylbenzene sulfonates in which the alkyl group contains from about 9 to 15 carbon atoms; polyhydroxy fatty acid amides of the formula;

wherein R is a $C_{9-17}$ alkyl or alkenyl, $R_1$ is a methyl group and Z is glycidyl derived from a reduced sugar or alkoxylated derivative thereof; or mixtures thereof;
      (ii) from about 0.1% to 80% by weight of a detergent builder; and
      (iii) from about 0.01% to 50% by weight of a dispersible polyolefin; and
   b) adding said laundry detergent composition to the wash cycle of a laundry process such that said laundry detergent composition contacts the fabric that is being washed during the wash cycle.

13. The method of claim 12 wherein said dispersible polyolefin is emulsified with anionic surfactant, nonionic surfactant, or a mixture thereof.

14. The method of claim 12 wherein said dispersible polyolefin has a wax dropping point of from about 30 to 150° C.

15. The method of claim 12 wherein said dispersible polyolefin has an acid number from about 5 to 200 mg/g KOH.

* * * * *